(12) United States Patent
Edoga et al.

(10) Patent No.: US 8,496,700 B2
(45) Date of Patent: Jul. 30, 2013

(54) AORTIC VALVE REPLACEMENT

(75) Inventors: John K. Edoga, North Beach, NJ (US);
Thierry Richard, Florham Park, NJ (US)

(73) Assignee: Edrich Health Technologies, Inc., Morristown, NJ (US)

( * ) Notice: Subject to any disclaimer, the term of this patent is extended or adjusted under 35 U.S.C. 154(b) by 858 days.

(21) Appl. No.: 12/293,944

(22) PCT Filed: Mar. 23, 2007

(86) PCT No.: PCT/US2007/007305
§ 371 (c)(1),
(2), (4) Date: Oct. 23, 2009

(87) PCT Pub. No.: WO2007/112029
PCT Pub. Date: Oct. 4, 2007

(65) Prior Publication Data
US 2010/0049312 A1 Feb. 25, 2010

Related U.S. Application Data

(60) Provisional application No. 60/784,982, filed on Mar. 23, 2006.

(51) Int. Cl.
*A61F 2/24* (2006.01)
(52) U.S. Cl.
USPC ....... 623/2.11; 623/1.24; 623/2.14; 623/2.38; 623/1.22; 606/185; 606/170; 606/219

(58) Field of Classification Search
USPC .............. 623/2.11, 1.24, 2.38, 2.14; 606/185, 606/219
See application file for complete search history.

(56) References Cited

U.S. PATENT DOCUMENTS

| 7,041,132 | B2 | 5/2006 | Quijano et al. |
| 7,311,730 | B2 * | 12/2007 | Gabbay ........................ 623/2.38 |
| 7,331,991 | B2 | 2/2008 | Kheradvar et al. |
| 2004/0034380 | A1 | 2/2004 | Woolfson et al. |

* cited by examiner

*Primary Examiner* — Vy Q Bui
(74) *Attorney, Agent, or Firm* — Day Pitney LLP

(57) ABSTRACT

A device for replacement of a bioprosthetic valve having an annulus (104) and one or more leaflets (105), the device having an outer housing (106) and an inner shaft (108) with a distal end (110). The outer housing (106) is slideable relative to the inner shaft (108) such that a portion of the inner shaft (108) may be revealed. A cap (112) is associated with the distal end (110) of the inner shaft (108), the cap (112) movable between a first position adjacent the inner shaft (108) and a second position displaced from the inner shaft (108). The cap (112) is adapted to trap a skirted valve frame (102) between said cap (112) and the inner shaft (108) when in the first position. The skirted valve frame (102) may be released by the cap (112) upon sliding of the outer housing (106) relative to the inner shaft (108) to reveal the inner shaft (108) and upon movement of the cap (112) to the second position. Also disclosed are associated methods.

21 Claims, 8 Drawing Sheets

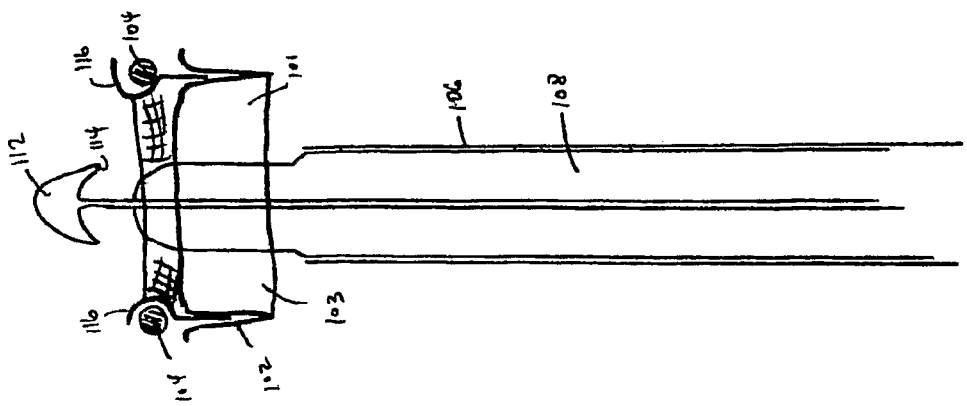
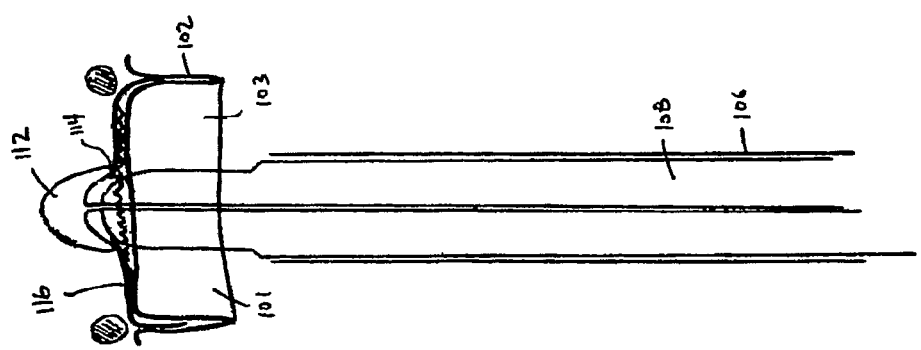
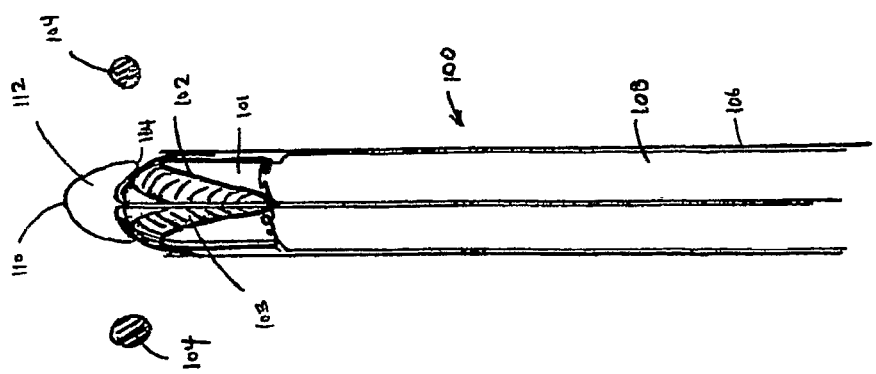

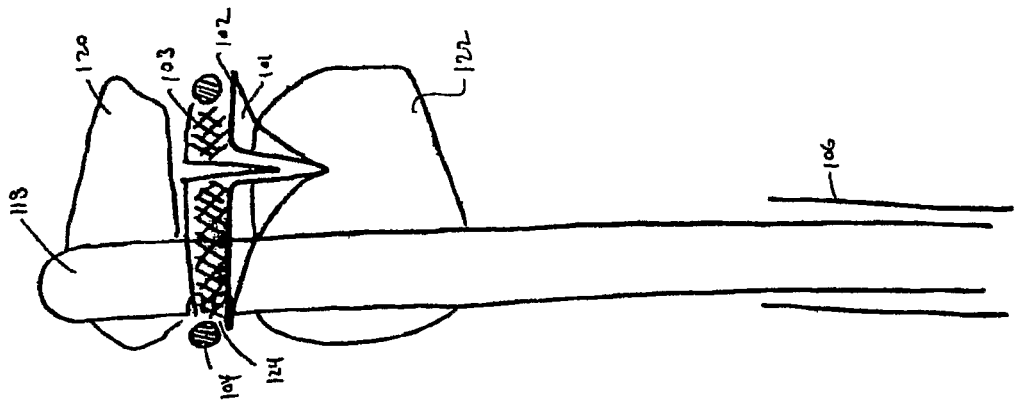
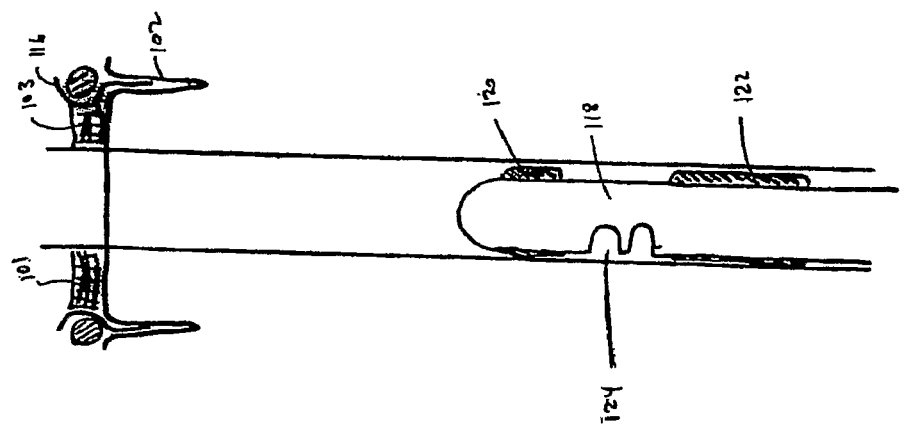
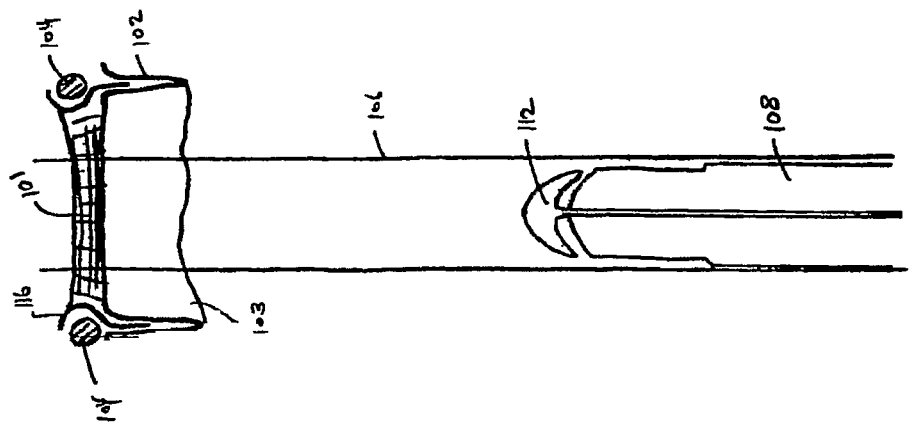

AORTIC VALVE REPLACEMENT

CROSS REFERENCE TO RELATED PATENT APPLICATION

The present application claims the benefit of the filing date of U.S. Provisional Patent Application No. 60/784,892 filed Mar. 23, 2006, the disclosure of which is hereby incorporated herein by reference.

BACKGROUND OF THE INVENTION

Previous patent applications by the inventors herein, including U.S. application Ser. Nos. 10/737,466 and 10/837,827, and related applications, which are all incorporated by reference herein in their entireties, disclose and relate to a stapling device for use in the fixation of endovascular grafts to the walls of vessels. The present disclosure builds on those teachings by providing, in accordance with certain aspects, novel valve structures and surgical instruments for replacing a failing bioprosthetic aortic valve using a minimally invasive transvascular approach. The present disclosure also discloses methods for replacing a failing bioprosthetic aortic valve using a minimally invasive approach. The disclosure utilizes not only staplers of the type described in the previously referenced applications, but additional devices which are novel to the present disclosure.

More specifically, this invention relates to structures, methods and stapling devices for replacement of bioprosthetic aortic valves. The replacement structures, methods, and stapling devices facilitate the rapid durable joining of a new aortic valve to the annulus structure of a preexisting damaged bioprosthetic aortic valve with significantly reduced risk to the patient as compared to conventional surgical open heart methods.

Many patients who suffer from severe aortic valve disease have undergone surgery to replace their original aortic valve in order to restore proper cardiac function. Such replacement bioprosthetic valves may be commonly formed from porcine aortic valves or modified bovine pericardium, each of which have been used in many cases in the presence of certain indications. Such indications include patient age over 70, contraindication to lifelong systemic anticoagulation, or because of the known lower rates of thromboembolic complications associated with these types of valves.

Bioprosthetic valves, however, have diminished durability compared to mechanical valves and frequently fail during the patient's lifetime because of stenosis due to leaflet fusion and or calcification, or incompetence due to leaflet tears and degeneration. Subsequent surgical intervention to replace these failed valves is associated with very high morbidity and mortality rates because of the generally poor medical condition of the subjects. This makes it necessary to seek less intrusive methods to achieve this valve replacement. The present invention provides for a less invasive option for replacing a failing bioprosthetic aortic valve while addressing the need to actively fix the replacement valve so that it is not moved by the pressure of blood flow. Attempts to hold these new valves in place using stents have not provided durable results for obvious reasons.

BRIEF SUMMARY OF THE INVENTION

In accordance with one aspect of the invention, a device for a device for replacement of a bioprosthetic valve having an annulus and one or more leaflets comprises an outer housing, an inner shaft having a distal end, the outer housing slideable relative to the inner shaft such that a portion of the inner shaft may be revealed, a cap associated with the distal end of the inner shaft, the cap movable between a first position adjacent the inner shaft and a second position displaced from the inner shaft, the cap adapted to trap a skirted valve frame between the cap and the inner shaft when in the first position, wherein the skirted valve frame may be released by the cap upon sliding of the outer housing relative to the inner shaft to reveal the inner shaft and upon movement of the cap to the second position.

The trapped skirted valve frame may comprise a shape memory alloy.

The cap may comprise hooks retaining the trapped skirted valve when in the first position.

The trapped skirted valve may be partially released when the outer housing is slid to reveal the inner shaft and the cap is in the first position.

The inner shaft may be completely removed from within the outer housing.

In accordance with further aspects of the present invention, a bioprosthetic replacement valve may comprise a valve frame formed from memory metal, a skirt operatively engaged with the valve frame, securing members attached to the valve frame and formed from memory metal, wherein the valve may be introduced into the annulus of a previously installed bioprosthetic valve and secured thereto with the securing members.

The valve may further comprise a plurality of leaflets.

In accordance with another aspect of the present invention, a delivery system for attachment of a bioprosthetic aortic valve to the annulus of a previously installed bioprosthetic aortic valve may comprise a valve replacement instrument, the instrument having an outer housing adapted to be inserted within an aortic root toward the previously installed bioprosthetic valve and an inner shaft, the outer housing having a first position concealing the inner shaft and a second position revealing at least a portion of the inner shaft, a bioprosthetic replacement valve having a valve frame and a skirt operatively engaged to the valve frame, the bioprosthetic replacement valve trapped between the inner shaft and the outer housing in the first position of the outer housing.

The bioprosthetic replacement valve may be released from between the inner shaft and the outer housing in the second position of the outer housing.

The bioprosthetic replacement valve may further comprise a plurality of securing members for association with the annulus of a previously installed bioprosthetic aortic valve upon positioning of the outer housing in the second position. If so configured, the securing members may be hooks.

The frame of the bioprosthetic replacement valve may be formed from a memory metal.

The inner shaft may be removed from the outer housing. If so configured, the delivery system may further comprise a stapler adapted to be inserted within the outer shaft, the stapler adapted to attach the bioprosthetic replacement valve to the annulus.

The valve replacement instrument may further comprise a cap associated with the inner shaft, the cap further trapping the folded valve in the first position of the outer housing.

In accordance with still further aspects of the present invention, a method of replacing a previously installed bioprosthetic aortic valve having leaflets and an annulus may comprise preparing the leaflets for replacement, inserting a valve delivery instrument into the aortic root, the valve delivery instrument including a folded replacement valve having securing members formed from a memory metal, positioning the valve delivery instrument such that the folded replacement valve is adjacent to the annulus of the previously installed bioprosthetic valve, releasing the folded valve from the valve delivery instrument such that the securing members return to their natural condition and connect to the annulus, removing an inner portion of the valve delivery instrument, inserting a stapler into the remaining portion of the valve delivery instrument, positioning the stapler adjacent to the annulus, stapling the valve to the annulus.

The step of preparing the leaflets for replacement may involve destroying the leaflets.

The step of stapling the valve to the annulus may involve multiple staples.

The stapler may further comprise at least one balloon, the method further comprising the step of inflating the at least one balloon.

The folded replacement valve may include a frame formed from a memory metal.

The folded replacement valve may include a skirt attached to the frame, the step of stapling the valve involving stapling the skirt of the valve to the annulus.

The step of releasing the folded valve may open the skirt and apply it against the annulus.

BRIEF DESCRIPTION OF THE DRAWINGS

The subject matter regarded as the invention is particularly pointed out and distinctly claimed in the concluding portions of the specification. The invention, however, both as to organization and method of operation, together with features, objects, and advantages thereof will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claim.

In regard to the drawings,

FIG. 1 is a sagittal section of an aortic root with a valve delivery instrument having a replacement valve in a folded position within a delivery sheath in an initial position in accordance with one embodiment of the present invention;

FIG. 2 is a sagittal section of the aortic root with the valve delivery instrument of FIG. 1 and replacement valve in a deployed position;

FIG. 3 is a sagittal section of the aortic root with the valve delivery instrument of FIG. 1 and replacement valve in a deployed and the memory metal retaining hooks in a released position;

FIG. 4 is a sagittal section of the aortic root with the valve delivery instrument of FIG. 1 being removed and the replacement valve in a deployed and released position;

FIG. 5 is a sagittal section of the aortic root with the replacement valve in a deployed and released position and a stapler being inserted;

FIG. 6 is a sagittal section of the aortic root with the replacement valve in a deployed and released position and the stapler's intracardiac and aortic root balloons inflated;

DETAILED DESCRIPTION

Figure 8:
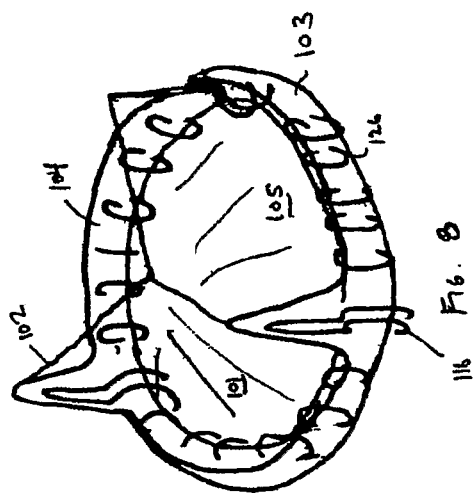
FIG. 8 is an isometric view of the replacement valve stapled to the annulus.

In the following is described the preferred embodiments of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

One aspect of the present invention concerns the replacement of a bioprosthetic aortic valve using a minimally invasive transvascular approach. In order to provide such a replacement, the leaflets of the prior bioprosthetic valve may be destroyed and pushed aside using for example, an appropriately sized non compliant balloon. Once the area is cleared, a valve 101 supported on a memory metal frame 102 sized to fit into the annulus 104 of the prior bioprosthetic valve may be delivered to the site using standard catheter techniques.

It is preferred that the replacement valve 101 be configured from a plurality of modified bovine pericardium leaflets associated with a stented valve frame 102 having a skirt 103 of durable, biocompatible fabric such as a polyester fabric or polytetrafluoroetylene (PTFE) fabric attached to the base of the stented frame 102. It is preferred that the stented valve frame 102 be formed from Nitinol, or other suitable memory alloys (also referred to as memory metals). The assembly also preferably includes a plurality of memory alloy (e.g. Nitinol) hooks 116 or securing members which, when released, return to their natural form or condition around the rim of the annulus 104, thus applying the fabric skirt 103 to the annulus 104 while the valve leaflets sit in a supra annular position. The application of the fabric over the "crushed" old valve leaflets serves an additional purpose of keeping potential fragments from embolizing into the blood stream.

A specialized endovascular stapler 118 utilizing methods of the type generally disclosed in the previous applications for staple closure employing W-shaped staples (referenced above) may be used to fasten the fabric skirt 103 to the annulus 104. This specialized stapler 118 preferably comprises two asymmetric semi-compliant balloons 120, 122, whereas previously disclosed staplers comprised only a single balloon. A distal balloon 120 may be located within the heart during the stapling cycle. When inflated and pulled back, the distal balloon 120 may position the staple exit area 124 of the stapler 118 at the approximate level of the annulus 104. A proximal balloon 122 may then be inflated to bias the stapler 118 against the rim of the annulus 104 to ensure purchase between the stapler, and annular rim, when the staple 126 is fired. Inflation of the balloons 120, 122 insures proper location of the staple exit area 124 and proper purchase such that each staple 126 fired forms a permanent connection between the rim of the annulus 104 and the skirt 103. Thus, the valve 101 may be installed in a reliable and repeatable manner insuring longevity of the desired connection. It will be appreciated that each balloon 120, 122 may be inflated with a suitable liquid such as dilute contrast or saline. It will also be appreciated that the balloons 120, 122 are preferably configured so as not to fully occlude blood flow.

Throughout the stapling cycle, as shown in the attached illustrations, the valve 101 leaflets are preferably kept in an open position and out of the path of the staples using either the outer housing 106 or the stapler 118 and its balloon systems 120, 122. It is particularly important to avoid damaging the valve leaflets during the valve replacement operation and in particular, the stapling operation.

Delivery of the stented valve in accordance with certain aspects of the invention is shown in FIGS. 1 through 4. These steps may be completed once the leaflets of the prior bioprosthetic valve are destroyed and pushed aside through the use of a non-compliant balloon. In this regard, an appropriately sized non-compliant balloon may be inserted through an R subclavian access and positioned between the valve leaflets. The balloon may then be inflated to a high pressure up to 12 atmospheres. This crushes the valve leaflets and opens the space, albeit smaller, for a new valve. An anti-embolism protection device commonly used for carotid angioplasty may be used to trap any loose fragments. It will be appreciated that during the time of balloon inflation, cardiac output is diminished by cardiac pacing.

As shown in FIG. 1, a sagittal section of the aortic root, a valve delivery instrument 100 may deliver a valve 101 having a valve frame 102 supporting a skirt 103 and leaflets 105 (FIG. 8) to the annulus 104 of the previously installed bioprosthetic valve. The instrument 100 may include a hollow outer housing 106 with an inner shaft 108 therein. The inner shaft 108 may culminate at the distal end 110 of the instrument 100 with a cap 112 having three pairs of hooks 114. The valve 101, including the valve frame 102, the skirt 103, and the leaflets 105, is preferably contained within the instrument during the initial stages of delivery to the replacement site by the cap 112 and hooks 114. The cap 112 and hooks 114 engage and maintain the valve 101 in a folded position during insertion of the instrument 100 and positioning at the valve replacement site.

The valve frame 102 is preferably made from a shape memory alloy material. A shape memory alloy (SMA, also known as a smart alloy or memory metal) is a metal that "remembers" its geometry. After a valve mounted on a SMA frame has been deformed from its original configuration, for example by folding the valve 101 for loading in the deployment instrument and securing of the valve in the folded condition by the cap 112, it regains its original geometry by itself, simply by the release of the forces applied by the cap 112. One memory metal material of choice is Nitinol (an acronym for NIckel TItanium Naval Ordnance Laboratory), because in addition to its exhibiting unique SMA behavior, it is also known to be biocompatible. Other biocompatible SMA's may also be utilized.

As shown in FIG. 2, the valve frame 102 may be deployed from the instrument by withdrawing the outer housing 106 relative to the inner shaft 108. Typically, withdrawal of the outer housing 106 may be achieved by an operator securing the inner shaft 108 with one hand while pulling back on the outer housing 106. Other methods may also be utilized, such as rotational devices which impart relative movement between the inner shaft 108 and outer housing 106.

Upon withdrawal of the outer housing 106, the valve frame 102 is free to extend to its natural condition by nature of the memory alloy utilized for its construction and the lack of restraint previously provided by the outer housing. Each securing member 116, also preferably manufactured from a memory alloy such as Nitinol, continues to be retained by the cap 112 on one end while being extended outwardly due to its connection with the valve frame 102 on the other end, as shown in FIG. 2.

In a subsequent step, the cap 112 may be advanced by a trigger mechanism as discussed below and separated from the inner shaft 108 to fully release the securing members 116. As shown in FIG. 3, the securing members 116 will return to their natural condition partially wrapping around the annulus 104, to temporarily support the valve frame 102 in relation to the annulus 104, once the cap 102 is advanced. This step serves to attach the valve 101 to the annulus 104 by hooking the skirt 103 of the valve 101 to the annulus.

The inner shaft 108 with cap 112 may then be withdrawn from within the outer housing 106, as shown in FIG. 4, clearing away room for insertion of a specialized endovascular stapler 118.

The stapler 118 is shown being inserted into the outer housing in FIG. 5. As shown, the stapler 118 includes a distal intracardiac balloon 120 and a proximal aortic balloon 122 bracketing a staple exit area 124.

The stapler 118 may be advanced toward the distal end 110 of the instrument 100 until the staple exit area 124 is adjacent to the annulus 104 of the prior valve, at the lumen of the replacement valve 101. The stapler's 118 leading elements are advanced to the position required for securing the valve 101 to the annulus 104 which should be accurately identified. The annular material may be densely radio opaque or such identification may be conducted by utilizing an ultrasonic probe or other known location method.

The outer housing 106 may then be withdrawn and the balloons 120, 122 inflated, as shown in FIG. 6. It will be appreciated that inflation of the balloons is preferably achieved by inflating the intracardiac balloon 120 first, with the stapler 118 then pulled back gently to engage the annulus 104 before the aortic balloon 122 is inflated. The combination of the two balloons 120, 122 serve to abut the staple exit area 124 against the annulus 104 so a good purchase may be made with a staple 126 deployed through the staple exit area 124. It will be appreciated that the balloons 120, 122 are designed such that they do not completely occlude the aortic lumen. Such balloons may, for example, be V-shaped for this purpose.

Figure 7:
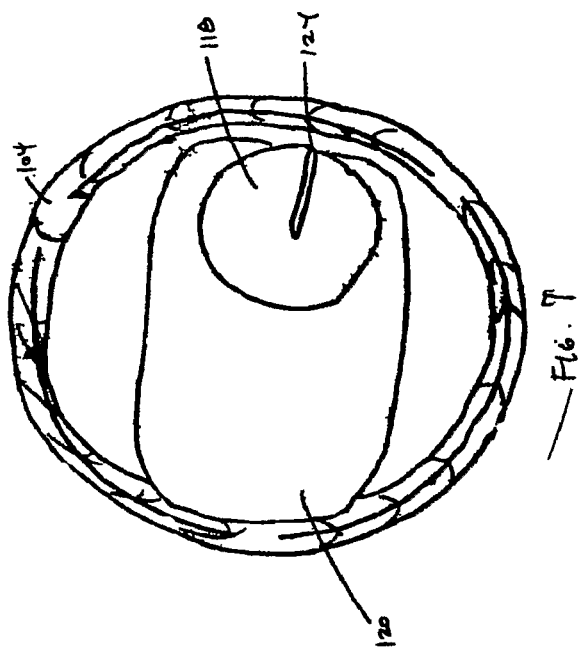
FIG. 7 is top-view of the stapler of FIG. 5 with inflated intracardiac balloon next to the annulus prior to stapling.
Figure 13A:
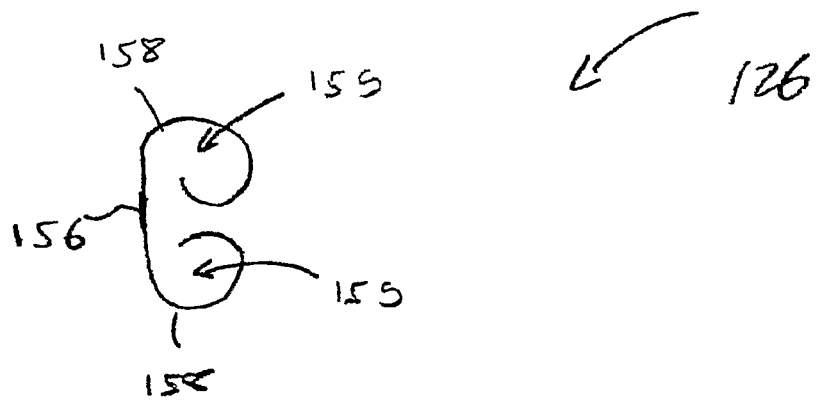
FIG. 13A is a side view of the staple of FIG. 8 in its closed condition.
Figure 13B:
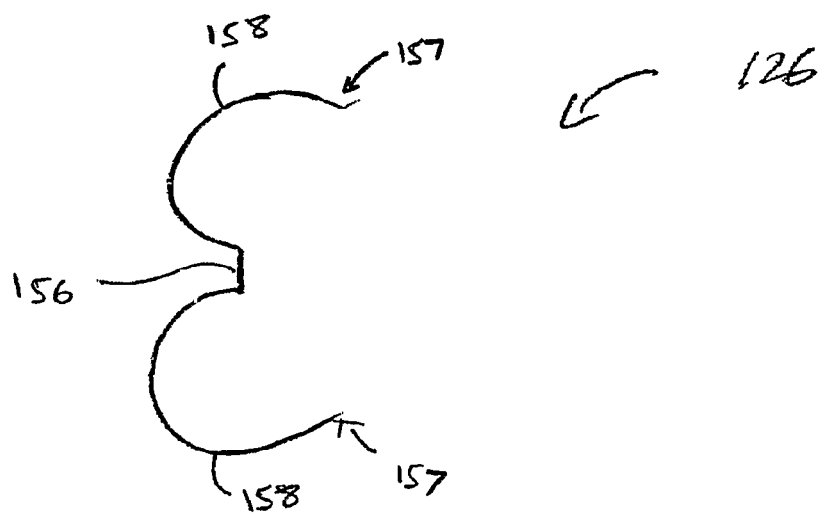
FIG. 13B is a side view of the staple of FIG. 8 in its open condition; and, FIG. 14 depicts a cut-away perspective view of a stapler housing which may form a portion of a stapler of the type shown in FIG. 12.

FIG. 7 depicts a top-view of the stapler 118 and intracardiac balloon 120 within the annulus 104, just prior to deployment of any staples. It will be appreciated that the staples 126 may be deployed through the staple exit area 124 where they are formed into hooks, circles, partial hooks, partial circles, or the like. In this regard, a single stroke of the stapler trigger (described below) preferably causes forward displacement of a staple pusher sufficient to advance a single staple through valve 101 and the annulus 104. In preferred embodiments, the staples are W-shaped while in the stapler and deformed into B-shape upon deployment, as shown in FIGS. 13A and 13B. The staples are preferably configured from biocompatible materials, and particularly biocompatible metals, such as stainless steel or titanium.

Figure 14:
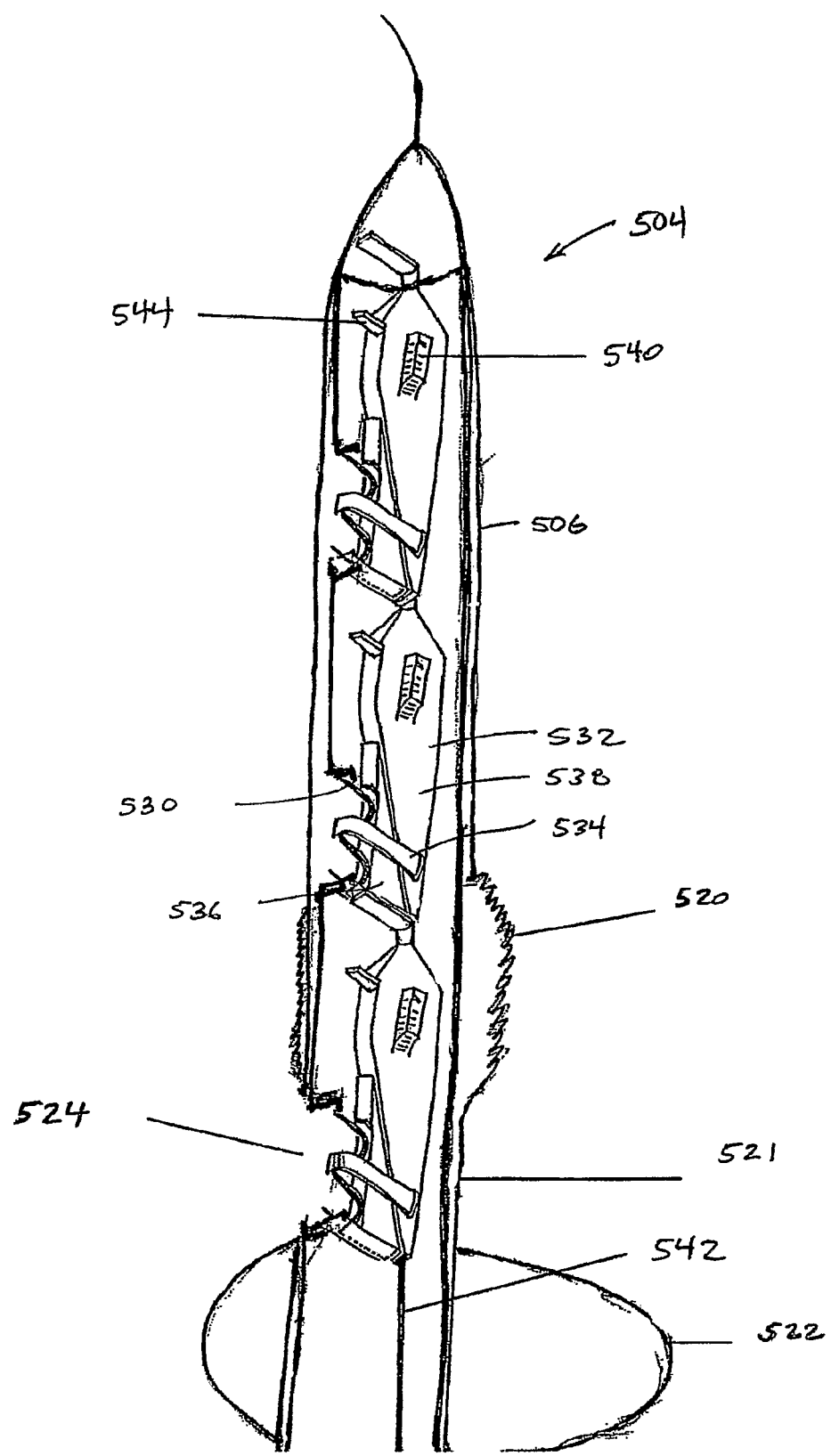

Staples may be stored within a cartridge in the stapler 118 such that multiple staples may be deployed consecutively as the stapler 118 is rotated around the 360 degrees of the annulus 104. The staples, pushers, and actuators may also be stacked end-to-end in a cartridge at the distal end of the stapler as shown in FIG. 14. In such case, the next staple in line is pulled down to the staple exit area when the stapler has been rotated to the next location to be stapled. In order to rotate the stapler 118 for next deployment, the balloons 120, 122 may be partially deflated and then re-inflated when the staple exit area 124 is positioned for next deployment.

Although the number may vary, it is preferred that between 9 and 12 staples be utilized to properly secure the valve 101. Once all staples have been deployed, the stapler 118 may be retracted completely, to leave the valve frame 102 attached to the annulus as shown in FIG. 8.

Figure 9:
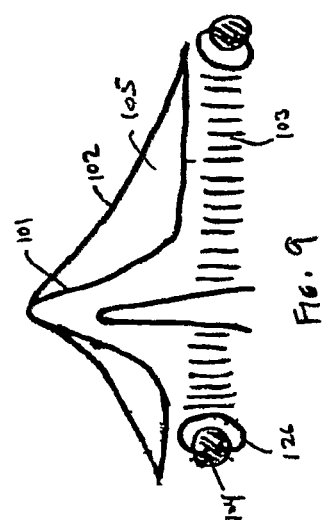
FIG. 9 is cross-sectional view of the replacement valve of FIG. 8.

As shown in FIG. 8, staples 126 are deployed to further support the valve frame 102 and skirt 103, where the staples 126 penetrate the valve 101 and previously installed annulus 104. A cross-section of this arrangement can also be seen in FIG. 9.

Figure 10:
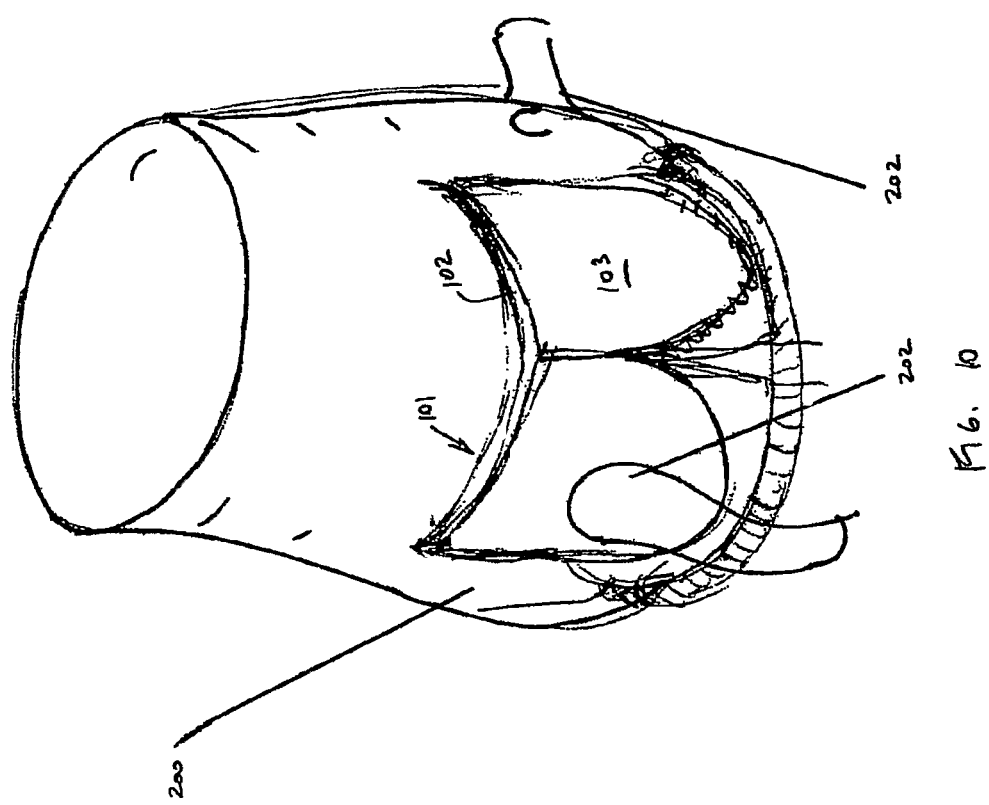
FIG. 10 is perspective view of the aortic root and coronary arteries with the replacement valve installed.

FIG. 10 depicts a perspective view of the aortic root 200 and coronary arteries 202 with the replacement bioprosthetic valve 101 fully installed. It will be appreciated that the stapling methods of fixation of the aortic valve do not interfere with the coronary artery sinuses.

Figure 11:
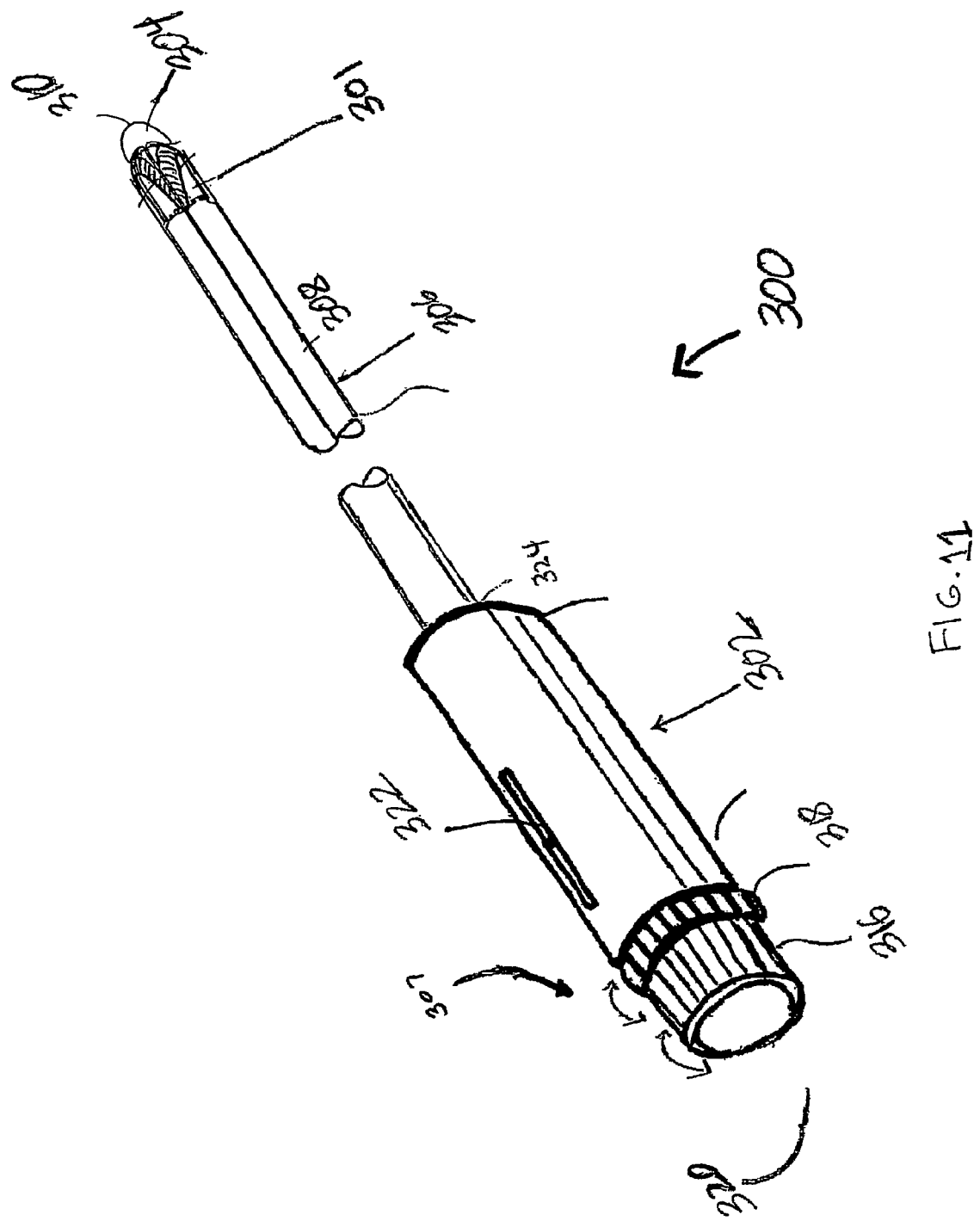
FIG. 11 is a perspective view of a valve delivery instrument in accordance with an embodiment of the present invention.

FIG. 11 depicts a perspective view of a valve delivery device 300, in accordance with certain aspects of the present invention. The exemplary valve delivery device 300 may be utilized as the valve instrument 100, previously discussed. Of course, it will be appreciated that other similar devices may also be utilized.

As is shown, the device 300 may comprise a trigger housing or handle 302 located at the proximal end 307 of the device and a cap 304 located at the distal end 310 of the device. An inner shaft 308 within an outer housing 306 provides a connection between the trigger housing 302 and the cap 304. The trigger housing 302 may include a first trigger 316 and a second trigger 318 located toward a front portion 320 of the housing 302, at the proximal end 307 of the device. The triggers 316, 318 are concentrically arranged and capable of rotating about a longitudinal axis of the trigger housing 302. The first trigger 316 is part of a valve release mechanism configured to release the cap 310 from the valve 301 as explained below. The second trigger 318 is part of a housing actuation mechanism configured to actuate the advancement and retraction of the inner shaft 308 relative to the outer housing 306 as explained below in further detail.

In one embodiment, the trigger 316 is a dial capable of being turned in a first direction a predetermined amount, such as a quarter-turn, to cause the cap 304 to advance away from the distal end 310 of the device 300. The trigger 316 can be rotated in a second direction a predetermined amount, preferably the same predetermined amount (e.g. a quarter-turn), to retract the cap back toward the distal end 310 of the device 300. In other embodiments, the trigger 316 can be turned in other increments such as one-half and three-quarters, or other increments, to achieve the requisite advancement or retraction of the cap.

The second trigger 318 can be a dial capable of being rotated a predetermined amount in a first direction to cause the outer housing 306 to retract into an opening 324 formed within the handle 302. Other mechanical means can be used such as triggers, sliders, or collars, to perform equivalent functions to those of the dials. Such devices provide manual means for actuation of the various device 300 components.

Notwithstanding, it is also contemplated that an automatic means of actuating the components of the device 300 may also be utilized. For example, a computer controlled actuator device can be programmed to perform such functions.

The trigger housing or handle 302 also can include an indicator 322 which provides a visual indication of the number position or displacement of the cap 304 and/or outer housing 306 relative to the distal end 310 of the device 300. The indicator 322 is operatively coupled to the cap 304 and/or outer housing 306, or the associated trigger or other actuation mechanism, so as to track the position of the cap 310 and/or outer housing.

Figure 12:
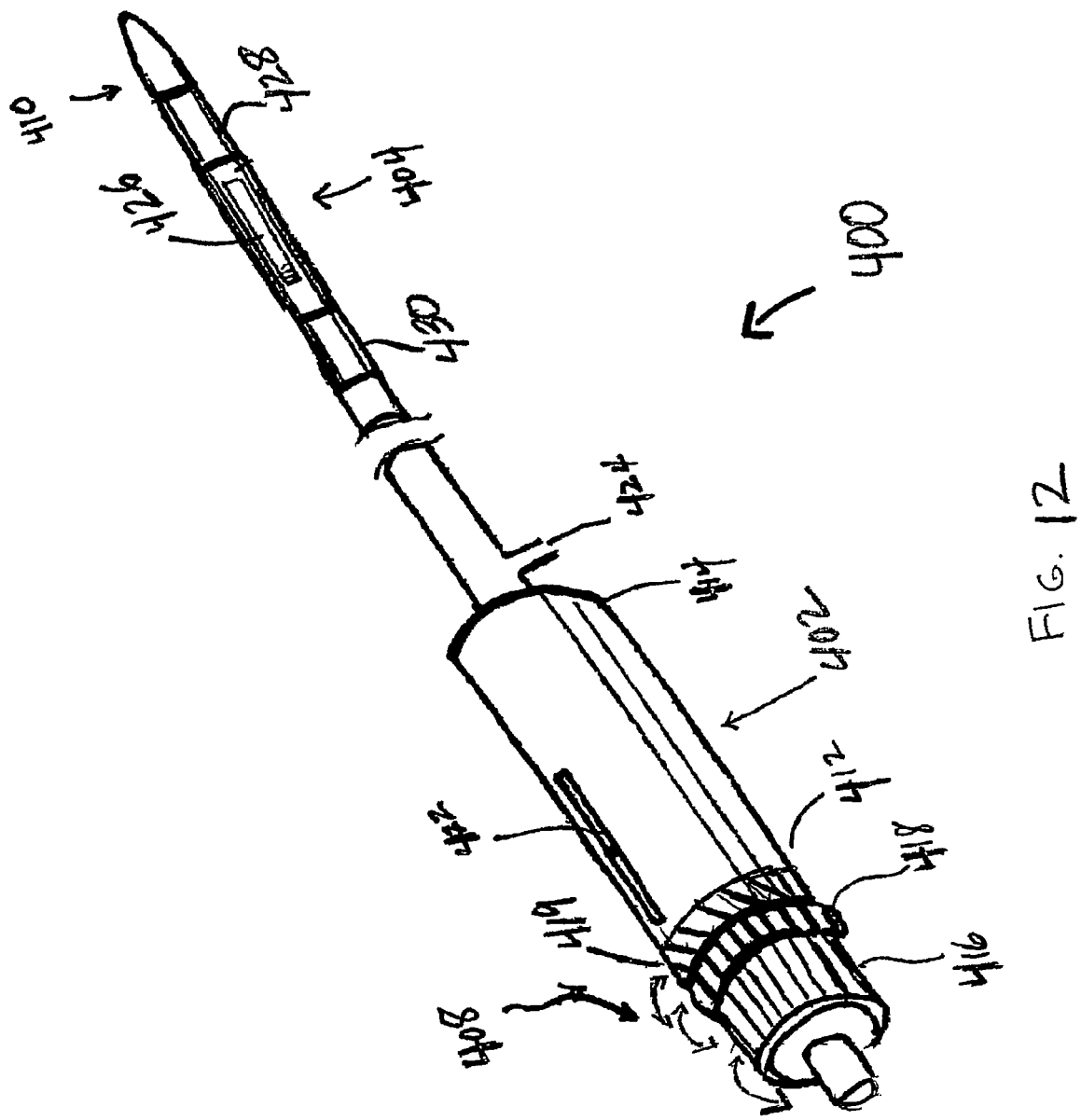
FIG. 12 is a perspective view of a stapler in accordance with an embodiment of the present invention.

FIG. 12 depicts a stapler 400 in accordance with certain aspects of the present invention. The exemplary stapler 400 may be utilized as the stapler 118, previously discussed. Of course, it will be appreciated that other similar devices may also be utilized.

As is shown in FIG. 12, the stapler 400 may comprise a trigger housing or handle 402 located at the proximal end 408 of the stapler 400 and a stapling mechanism or housing 404 located at the distal end 410 of the stapler. The trigger housing 402 may include a first trigger 416, second trigger 418, and third trigger 419 located toward a front portion 412 of the housing 402, at the proximal end 408. The triggers 416, 418, 419 are concentrically arranged and capable of rotating about a longitudinal axis of the trigger housing 402. The first trigger 416 is part of a staple actuation mechanism configured to actuate the discharge of staples from the staple housing 404 through staple exit area 426 as explained below. The second and third triggers 418, 419 are part of a displacement mechanism configured to actuate the expansion and retraction of a first distal balloon 428 and a second proximal balloon 430.

In one embodiment, the trigger 416 is a dial capable of being turned a predetermined amount, such as a quarter-turn, to cause a staple to be discharged from the staple exit area 426 of the staple housing 404. Following rotation of the stapler 400 into alignment for the firing of a second staple (and associated deflating and inflating of the balloons), the trigger 416 can be rotated again to discharge a second staple. In other embodiments, the trigger 416 can be turned in other increments such as one-half-turn or three-quarter-turn, or other increments.

The second and third triggers 418, 419 are part of a displacement mechanism configured to actuate the expansion and retraction of a first distal balloon 428 and a second proximal balloon 430. In one embodiment, the second trigger and third triggers 418, 419 can be a dial capable of being rotated a predetermined amount in a clockwise first direction to cause the respective balloons 428, 430 to expand or rotated in a second direction to cause the balloons to collapse. It will be appreciated that the stapler 400 includes a pair of fluid ports 424 adapted to connect to liquid storage bags for storing the balloon inflation fluid when not within the balloon.

Other mechanical means can be used as trigger, such as sliders, collars, or other mechanisms, which can be used to perform equivalent functions to those of the dials.

Further, as explained above, the triggers 416, 418, 419 provide a manual means of actuating the various components of the stapling mechanism 404 such as the discharge of staples therefrom. However, it is contemplated that an automatic means of actuating the components of the stapler may be provided as an alternative. For example, a computer controlled actuator device can be programmed to perform such functions.

The trigger housing or handle 402 may also include an indicator 422 which provides a visual indication of the number of staples discharged. The indicator 422 may be operatively coupled to the first trigger 416 or staple pusher so to track the rotation of the first trigger or advancement of the staple pusher and thus the number of staples discharged.

FIGS. 13A and 13B show detailed views of an exemplary staple 126 used in the staplers 118 and 400 as depicted in FIGS. 5 and 12, respectively. Preferably, the staple 126 is constructed of a memory alloy such as Nitinol, as is commonly used in the art.

Within the staple housing 404 of the stapler 400 (FIG. 12), the staple 126 will typically be formed into the condition shown in FIG. 13B, or even further into a completely straight wire segment. Meanwhile, after discharge, the staple 126 will be deformed to the configuration shown in FIG. 13A.

Upon application into the valve skirt and annulus, the U-shaped sections 158 of the staple 156 may be bent into loops such that spiked ends 157 are adjacent to the central element 156. During the application process, the spiked ends 157 may pierce the valve skirt and annulus so as to securely attach the two together in as many locations as desired to permanently secure the replacement valve to the annulus.

FIG. 14 depicts a cut-away perspective view of a stapler housing which may form a portion of a stapler of the type shown in FIG. 12. Similar to those staplers previously discussed, the particular stapler housing 504 includes an outer housing 506 having a staple exit area 524. The stapler housing 504 also includes associated balloons, namely a distal balloon 520 and a proximal balloon 522. As shown in FIG. 14, the distal balloon includes an external balloon catheter 521, for supplying the balloon filling solution. It will be appreciated that internal catheters may alternatively be provided.

One features of stapler housing 504 is the ability to employ multiple staples 530. As shown in FIG. 14, the exemplary staple housing 504 includes three staples 530. Each of the staples 530 is associated with its own actuation device 532, which are stacked in tandem. The actuation devices employ a detent arm 534 which holds the respective staple 530 in place. Each actuation device 532 also includes a pusher 536 and a cam 538. Upon actuation of the actuation device, the pusher 536 is moved relative to the cam 538 forcing the staple 530 outward through the staple exit area 524. This action serves to form the staple 530 into its closed position from its open position within the stapler. Further actuation of the actuation device 532 serves to move a sloped protrusion 540 against the detent 534 to move the detent out of association with the staple, to release same. Upon release of one staple 530, a wire 542 may be pulled to move the next in the series of actuators into alignment with the staple exit area 524 for firing of the next staple. The wire may be pulled by an appropriate trigger, dial, or other mechanical means, or may simply be pulled by a user. It will also be appreciated that the actuators 532 each include an extension 544 which serves to displace the pusher 536 at the end of each firing stroke.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention has applicability in the field of medical devices.

The invention claimed is:

1. A delivery system for attachment of a bioprosthetic aortic valve to the annulus of a previously installed bioprosthetic aortic valve, the delivery systems comprising:
a valve replacement instrument, the instrument having an outer tubular housing adapted to be inserted within an aortic root toward the previously installed bioprosthetic valve; and
the outer tubular housing configured to receive an elongated body; the elongated body inserted into the inner cavity of the outer tubular housing;
a bioprosthetic replacement valve assembly assembled in a folded position and configured in the interior of the outer tubular housing and positioned around the lead end of the elongated body, the bioprosthetic replacement valve assembly having a valve frame and a skirt, the valve frame including at least one strut valve extension associated with at least one temporary fastener and at least one bioprosthetic leaflet, and the bioprosthetic replacement valve assembly being configured to be deployed from the outer tubular housing upon the retraction of the outer tubular housing permitting the bioprosthetic replacement valve assembly to expand and be positioned adjacent to the annulus of a previously installed bioprosthetic aortic valve; and
a displaceable cap configured to be advanced from the elongated body such that the at least one temporary fastener is unfolded and temporarily secures the valve assembly to the annulus of the previously installed bioprosthetic aortic valve;
wherein the elongated body and the displaceable cap are configured to be retracted from the inner cavity of the outer tubular housing to allow for the outer tubular housing to receive an endovascular stapler.

2. The delivery system of claim 1, wherein the bioprosthetic replacement valve assembly is configured to be released from the inner cavity of the outer housing.

3. The delivery system of claim 1, wherein the valve frame of the bioprosthetic replacement valve assembly is formed from a memory metal.

4. The delivery system of claim 3, wherein the at least one strut valve extension of the valve frame is formed from a memory metal.

5. The delivery system of claim 4, wherein the at least one valve strut extension is configured to assume the shape of a hook upon the advancement of the displaceable cap from the elongated body.

6. The delivery system of claim 3, wherein the end of the at least one temporary fastener is formed from a memory metal.

7. The delivery system of claim 1, wherein the stapler is adapted to permanently attach the bioprosthetic replacement valve assembly to the annulus of a previously installed bioprosthetic aortic valve via a plurality of staples.

8. The delivery system of claim 1, wherein a first trigger is associated with the displaceable cap.

9. The delivery system of claim 8, wherein the first trigger is configured to be actuated to cause the forward displacement of the displaceable cap from the elongated body.

10. The delivery system of claim 9, wherein the at least one temporary fastener is configured to be released from its collapsed position between the elongated body and the displaceable cap.

11. The delivery system of claim 8, wherein the displaceable cap is configured to be retracted into a locked position.

12. The delivery system of claim 8, wherein the outer tubular housing can be advanced over the elongated body to a position proximate the at least one bioprosthetic leaflet before the elongated body is retracted.

13. The delivery system of claim 8, further comprising a second trigger associated with the advancement or retraction of the outer tubular housing.

14. The delivery system of claim 1, wherein the valve replacement instrument is configured to be controlled by a computer.

15. The delivery system of claim 1, wherein the outer tubular housing includes an indicator that is configured to track the position of at lease one of (i) the cap and (ii) the outer tubular housing.

16. The delivery system of claim 1, wherein the displaceable cap is disposed at the distal end of the elongated body.

17. The delivery system of claim 1, wherein the skirt includes biocompatible fabric.

18. The delivery system of claim 17, wherein the skirt is configured to attach to the cardiac end of the valve assembly.

19. The delivery system of claim 18, wherein the skirt is positioned between the outer housing and the at least one valve strut extension.

20. The delivery system of claim 1, wherein the at least one valve strut extension is configured to act as at least one temporary fastener.

21. The delivery system of claim 20, wherein the at least one valve strut extension is positioned on the inner surface of the skirt.

\* \* \* \* \*